United States Patent [19]

Thorjusen, Jr.

[11] Patent Number: 4,730,936
[45] Date of Patent: Mar. 15, 1988

[54] GAS DRIVEN SYSTEM FOR PREPARING LARGE VOLUMES OF NON-OXIDIZED, PYRIDOXYLATED, POLYMERIZED STROMA-FREE HEMOGLOBIN SOLUTION FOR USE AS A BLOOD SUBSTITUTE

[75] Inventor: Philip S. Thorjusen, Jr., Ocean Springs, Miss.

[73] Assignee: The United States of America as represented by the Secretary of the Air Force, Washington, D.C.

[21] Appl. No.: 917,573

[22] Filed: Oct. 10, 1986

[51] Int. Cl.$^4$ .............................................. B01F 13/02
[52] U.S. Cl. ........................... 366/101; 261/DIG. 28; 366/137; 422/44
[58] Field of Search ............... 366/101, 106, 107, 150, 366/136, 137, 159, 166; 422/44; 210/198.1, 927; 520/380, 381, 385; 128/DIG. 22; 261/DIG. 28

[56] References Cited

U.S. PATENT DOCUMENTS

| | | | |
|---|---|---|---|
| 4,001,200 | 1/1977 | Bonsen et al. | 260/112.5 R |
| 4,136,093 | 1/1979 | Bonchard et al. | 260/112.5 R |
| 4,396,584 | 8/1983 | Burgess | 261/DIG. 28 |
| 4,440,722 | 4/1984 | Luppi | 261/DIG. 28 |
| 4,466,804 | 8/1984 | Hino | 422/44 |
| 4,529,719 | 7/1985 | Tye | 514/6 |
| 4,622,140 | 11/1986 | Lee | 422/44 |

OTHER PUBLICATIONS

R. E. Benesch et al., "Affinity Labeling of the Polyphosphate Binding Site of Hemoglobin", Biochemistry, vol. 11, No. 19, Nov. 1972, pp. 3576–3582.
R. P. Ten Eyck et al., "Stroma–Free Methemoglobin Solution: an Effective Antidote for Acute Cyanide Poisoning", American Journal of Emergency Medicine, vol. 3, No. 6, Nov. 1985, pp. 519–523.

Primary Examiner—Robert W. Jenkins
Attorney, Agent, or Firm—Fredric L. Sinder; Donald J. Singer

[57] ABSTRACT

An apparatus and method for reacting dilute concentrations of delicate bioorganics or other reactants without creating microconcentrations of reactant during the reaction process. The apparatus mixes reagents inside of Y-connector with flowing solution from a solution reservoir. The reagents are introduced through a stopcock controlled infusion port at the center of the Y-connector. Solution and pressurized gas are each supplied to one of the three legs of the Y-connector and the resulting mixed solution from the third leg of the Y-connector is lifted by bubbles of the pressurized gas to return to the solution reservoir. A gaseous separation unit is placed inside the solution reservoir wherein the bubble lifted and mixed solution is forced through a permeable membrane enclosed by a perforated bulb to return to the reservoir. The perforated bulb is enclosed inside an additional enclosure having an opening below the solution level of the reservoir so that the returning solution will flow beneath the opening to the larger reservoir area and the excess gas will escape above the solution level through vent holes in the additional enclosure. Additional pressurized gas is delivered to the enclosure opening to bubble over the outside of the perforated bulb. A second Y-connector may be added between the first Y-connector and the solution reservoir.

11 Claims, 2 Drawing Figures

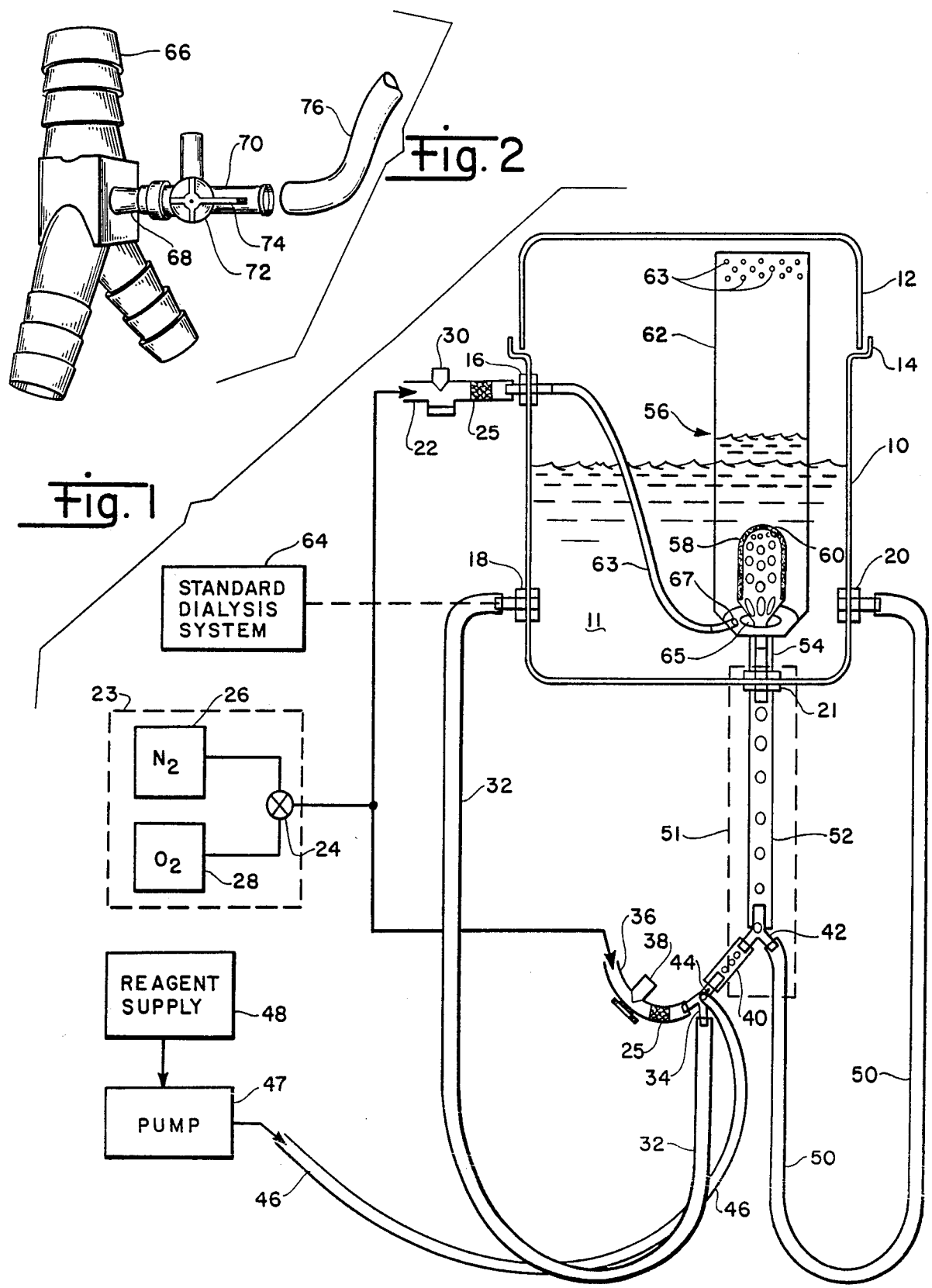

GAS DRIVEN SYSTEM FOR PREPARING LARGE VOLUMES OF NON-OXIDIZED, PYRIDOXYLATED, POLYMERIZED STROMA-FREE HEMOGLOBIN SOLUTION FOR USE AS A BLOOD SUBSTITUTE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to apparatus and methods for mixing chemicals, and more specifically to apparatus and methods that minimize production of unwanted byproducts when mixing dilute concentrations of chemicals.

Stroma-free hemoglobin solution, commonly referred to as SFHS, has been extensively studied for use as a whole blood substitute. SFHS is produced by removing all cell membrane components (i.e., stroma) from outdated human red blood cells. SFHS has advantages over whole blood in that it does not require cross-matching for blood type and may be safely stored for long periods. Unfortunately, when free of the stroma, hemoglobin, the oxygen-carrying component of blood cells, binds oxygen so tightly that its use for oxygen transport is severely compromised. Additionally, stroma-free hemoglobin has a short intravascular retention time in animals due to its small molecular size.

The prior art has discovered that SFHS can be modified to decrease the oxygen affinity of the hemoglobin and to polymerize the hemoglobin molecules to increase their size. The most widely used modification to decrease oxygen affinity reacts the hemoglobin with pyridoxal-5'-phosphate (PLP), as described by Benesch et al., in *Biochemistry*, Vol. 11, 3576 (1972). The most widely used modification to polymerize SFHS reacts the hemoglobin with a bifunctional cross-linking reagent such as gluteraldexyde. Detailed descriptions of both the process of making SFHS from whole blood and the subsequent modification of SFHS may be found in U.S. Pat. No. 4,136,093 to Bonhard et al. and in U.S. Pat. No. 4,001,200 to Bonsen et al.

Unfortunately, prior art processes for producing modified SFHS have not produced a product substantially free from undesirable byproducts and have not prevented the SFHS from oxidizing and producing undesirable levels of methemoglobin, a form of hemoglobin unsuitable for carrying oxygen. Additionally, the resulting molecular weights and other physical properties of the modified SFHS produced by prior art processes indicate that the desired chemical reactions have not been well controlled.

Modification of SFHS calls for very dilute concentrations of reagent to be mixed with SFHS. Prior art processes typically directly mix reagents with the SFHS to be modified, followed by agitating or stirring. This direct mixing results in micro-concentrations of reagents which produce the undesirable byproducts. While the prior art has discovered methods of removing these antigenic elements, those methods are after-the-fact and reduce the efficiency of the process. Thus it is seen that there is a need in the art for an improved apparatus and method that produces modified SFHS from previously prepared SFHS with a minimum production of undesirable byproducts and methemoglobin.

It is, therefore, a principal object of the present invention to provide an apparatus and method for modifying SFHS that produces minimum concentrations of undesirable byproducts and methemoglobin.

It is another object of the present invention to provide an apparatus and method for modifying SFHS that allows controlled reaction conditions which produce an uniformly consistent solution over extended periods of time.

It is yet another object of the present invention to provide a generalized apparatus and method for reacting dilute concentrations of delicate bioorganics without creating micro-concentrations of reactant during the reaction process.

It is a feature of the present invention that it provides a method for preparing large volumes of modified SFHS suitable for transfusion. If modified SFHS is chosen as a whole blood substitute for use in on-site treatment of major battlefield injuries, such large quantities will become necessary.

It is another feature of the present invention that it can be easily modified to produce, for example, methemoglobin from modified SFHS, which can then be further concentrated for use as a treatment in cyanide poisoning.

It is an advantage of the present invention that it provides a closed-loop system providing protection from environmental contamination.

It is another advantage of the present invention that all reactant materials are utilized with little waste, and production time is half that of other methods in use.

It is yet another advantage of the present invention that the chemical reactions are well controlled, eliminating the need found in much of the prior art for additional chemicals to stop reactions, and allowing tailoring of the physical properties of the resulting product to meet varying needs.

These and other objects, features and advantages of the present invention will become apparent as the detailed description of certain representative embodiments proceeds.

SUMMARY OF THE INVENTION

In accordance with the foregoing principles, objects, features, and advantages, the present invention provides a novel gas-driven, continuous flow, closed-loop apparatus and method for large-scale production of non-oxidized, pyridoxalated, altered stroma-free hemoglobin solution from stroma-free hemoglobin solution. Underlying the present invention is the recognition that direct mixing of reagents with SFHS produces micro-concentrations of reagent that produce undesirable byproducts and other effects. The unique discovery of the present invention is that bubbles can be used to both mix and circulate very dilute concentrations of reagent with solution. The bubbles are introduced to provide a site of high solution fluid activity for mixing, and then lift the mixed solution away from the mixing site to provide circulation. Additionally, the invention recognizes the problem that many bioorganics are highly reactive and provides a novel gaseous separation unit to separate the mixed solution from the bubbles while minimizing precipitation and the development of other unwanted byproducts.

Accordingly, the present invention is directed to an apparatus and method comprising reservoirs of solution and reagents, wherein the reagents are mixed with flowing solution at the center of a three fitting connector through a stopcock controlled infusion port. Solution from the solution reservoir and pressurized gas supply are each supplied to one of the three legs of the connector and the resulting mixed solution from the third leg of the connector is lifted by bubbles from the pressurized gas to return to the solution reservoir.

The invention also includes a second three fitting connector wherein the mixed solution from the first connector and additional solution from the solution reservoir are each supplied to one of the three legs of the second connector. The bubbles from the pressurized gas supply return the further mixed solution from the third leg of the second connector to the solution reservoir. The second connector may also be fitted with an infusion port and stopcock for the delivery of reagent to the flowing solution.

The invention further includes a gaseous separation unit inside the solution reservoir wherein the bubble lifted and mixed solution is forced through a permeable membrane enclosed by a perforated bulb to return to the reservoir of solution. The perforated bulb is enclosed inside an additional enclosure having an opening below the solution level through which the returning solution must travel to return to the larger solution reservoir, and smaller vent holes at the top above the solution level through which the excess gas escapes. Additional pressurized gas is delivered adjacent to the bottom opening where it bubbles over the outside of the membrane enclosing perforated bulb.

DESCRIPTION OF THE DRAWINGS

The present invention will be more clearly understood from a reading of the following detailed description in conjunction with the accompaning drawings wherein:

FIG. 1 is a schematic view of an apparatus for preparation of modified stroma-free hemoglobin incorporating the teachings of the present invention; and, FIG. 2 is a perspective view of a Y-connector having an infusion port and a stopcock.

DETAILED DESCRIPTION

Referring now to FIG. 1, there is shown a front view of an apparatus for preparation of modified stroma-free hemoglobin incorporating the teachings of the present invention. An enclosure 10, comprising a five-gallon fiberglass reservoir, holds the SFHS 11 to be modified. The enclosure has a cover 12 which fits over lip 14 so that pressurized gas may escape from inside the enclosure 10, while outside air is prevented from entering, thus helping to maintain a sterile environment for the SFHS. Enclosure 10 has four through-wall tube connectors 16, 18, 20, and 21. A hose 22 is connected to through-wall tube connector 16 on the outside of enclosure 10 and leads to a pressurized gas supply 23. Hose 22 is additionally fitted with an in-line sterile cotton filter 25. In this embodiment the pressurized gas supplied through hose 22 may be either $O_2$ or $N_2$, selected by a valve 24 connected to supplies 26, 28 of pressurized $N_2$ and pressurized $O_2$. Hose clamp 30 acts as a valve to regulate the flow of pressurized gas through through-wall tube connector 16. Another hose 32 is connected to through-wall connector 18 on the outside of enclosure 10 and loops below enclosure 10 to connect to one leg of Y-connector 34. A hose 36 connects to another leg of Y-connector 34 and leads to pressurized gas supply 23.

Hose clamp 38 regulated the flow of pressurized gas through Y-connector 34. Hose 36 includes another sterile in-line cotton filter. A tube 40 connects the remaining leg of Y-connector 34 to return apparatus 51 for return of solution and pressurized gas to enclosure 10. In this specific embodiment, apparatus 51 includes Y-connector 42 mounted above Y-connector 34. Y-connector 34 has at its center an infusion port into which is fitted a surgical 4-way stopcock 44. A solution administration tube 46 connects stopcock 44 with peristaltic pump 47. Chemical reagents desired to be mixed with flowing solution at Y-connector 34 are supplied from reagent supply 48 to pump 47.

To aid understanding of the operation of the apparatus of FIG. 1, FIG. 2 shows an enlarged view of an example Y-connector 66 having at its center an infusion port 68. Connected to the infusion port is an example surgical 4-way stopcock 70 having at its center a T-valve 72. Lever 74 controls the position of T-valve 72 and therefore the flow of liquids or gases through infusion port 68.

Another hose 50 is connected to through-wall connector 20 on the outside of the enclosure 10 and loops below the enclosure 10 to connect with a leg of Y-connector 42. The remaining leg of Y-connector 42 is connected by a vertical tube 52 to through-wall connector 21. A vertical tube 54 inside the enclosure 10 connects through-wall connector 21 to a gaseous separation unit 56. The gaseous separation unit 56 comprises a perforated plastic bulb 58 enclosing an inner layer 60 of foam or other permeable membrane. Holes forming the perforations in bulb 58 are relatively smaller toward the top of the bulb 58 and relatively larger toward the bottom. The gaseous separation unit 56 further comprises a cylindrical enclosure 62 having vent holes 63 about its upper end. Cylindrical enclosure 62 has an opening 65 in its base larger than the throat of bulb 58 so that solution may pass through the annular opening defined between the base opening and the throat of bulb 58. A hose 63 inside enclosure 10 connects through-wall connector 16 with a smaller opening 67 in the base of enclosure 62.

In operation, SFHS flows through hose 32 to one leg of Y-connector 34, where gas bubbles from pressurized gas provided from hose 36 lift the solution through tube 40 to a leg of Y-connector 42. Additional solution from hose 50 through another leg of Y-connector 42 is mixed with the solution from tube 40 and the combined solution is raised through tube 52 by the bubbles from tube 40.

Reagents to be reacted with the SFHS are slowly supplied by peristaltic pump 47 through the administration tube 46 connected to 4-way stopcock 44. The turbulence caused by the gas entering Y-connector 34 thoroughly mixes the reagents and rapidly moves the solution through Y-connector 34, preventing microconcentrations of reagent and the production of unwanted byproducts or uncontrolled reactions. The mixed solution is further mixed and diluted in Y-connector 42 with incoming solution from hose 50.

The gaseous separation system 56 removes the gas bubbles and returns the SFHS to the primary reservoir of SFHS inside enclosure 10. The separation of gas and liquid is performed primarily by the foam layer 60 as the solution is forced through it. Foam layer 60 is inside bulb 58 so that, among other reasons, the rigidity of bulb 58 prevents foam layer 60 from being blown out by solution pressure. This requirement may not exist in other embodiments and other advantages may be obtained by placing the foam layer over the bulb. The resistance of foam layer 60 to solution attempting to flow through it creates a backpressure that appears to increase the mixing effect in Y-connector 34 and 42. The bubbling of additional gas from opening 68 around the outside of bulb 58 helps prevent new reagent microconcentrations and prevents the buildup of a solid precipitate on the foam layer 60. The additional gas delivered inside cylindrical enclosure 62 also aids in forcing solution to return to the primary reservoir through the opening 65. Excess gas inside cylindrical enclosure 62 is released through vent holes 63 at its top. The gas released through vent holes 63 is vented to the outer atmosphere along lip 14. While operating, the water level in the gaseous separation system 56 rises above the solution level in the primary reservoir. The apparatus operates continuously, providing a constant flow of solution.

After preparation of a supply of solution has progressed to completion, through-wall connector 18 is used to drain the solution into a standard dialysis system 64 where final preparation of the SFHS may take place.

An improved understanding of the operation of the invention will be provided from study of the following example of the use of the disclosed apparatus to prepare modified stroma-free hemoglobin solution from unmodified SFHS. Unmodified SFHS may be obtained commercially, or may be prepared as taught in the cited prior art.

At least two days before starting modification of the SFHS, a supply of 1.0 Molar TRIS (hydroxymethyl)-aminomethane hydrochloride buffer (pH 7.4 at 4° C.) (TRIS HCl) was prepared. Previously obtained SFHS was stored in 1 liter blood storage bags at −27° C. To facilitate melting for use, the bags of SFHS were placed in water at room temperature and the resulting liquid poured into large sterile flasks in a cold room. A few milliliters of SFHS were checked with pH meter electrodes that had been standardized in a reference pH 7.0 phosphate buffer on ice to a pH of 7.09. All the apparatus for completion of the procedure was assembled and used in a 4° C. cold room.

TRIS HCl buffer was added to chilled SFHS from a 50 ml syringe with a 0.22 micron sterile filter. After reaching equilibrium in 20 minutes, the solution was adjusted to pH 7.4 +/−0.1, as necessary, by the dropwise addition of the previously prepared TRIS HCl or TRIS BASE (TRIS(hydroxymethyl)-aminomethane) buffer.

Next, pyridoxal 5-phosphate (PLP) was added to aid oxygen release to tissues. The amount of added PLP was four times the molar concentration of hemoglobin. This was obtained by taking the total hemoglobin in grams divided by the molecular weight of hemoglobin (65,000), times four, times the molecular weight of PLP (247.15). The total hemoglobin in grams was determined by multiplying the hemoglobin concentration in grams per deciliter by 10 to obtain grams per liter and then multiplying the resultant by the number of SFHS liters used. The PLP was dissolved in more of the previously prepared TRIS HCl buffer, and then added to the SFHS in the flask over a 15 minute period with constant stirring. 1-Octanol was added to the flask at 1 ml per liter of SFHS to prevent protein foaming. Finally, the mixture was poured into the enclosure 10 and the cover 12 set in place.

Nitrogen gas was then delivered through gas lines 22 and 36. Overnight degassing reduced the oxygen saturation value of the solution to less than 2%. Samples taken at Y-connector 34 through the 4-way stopcock 44 were placed inside test tubes with a mineral oil covering over the SFHS. A measurement of the hemoglobin concentration in those samples was used as the basis for calculating a new total hemoglobin content of the SFHS.

A reducing agent, sodium borohydride, was used to stabilize the chemical bond between pyridoxal 5-phosphate and the hemoglobin prior to alteration by glutaraldehyde. The number of grams of sodium borohydride ($NaBH_4$) required for this step was calculated using the total hemoglobin value divided by 65,000, multiplied by four (4 sites per heme molecule), multiplied by the molecular weight of $NaBH_4$ (37.83). The reducing agent was dissolved in 0.1 N sodium hydroxide (NaOH) at a concentration of 1 gm per 50 mls of base. While continuing delivery of nitrogen gas, two to four mls of this solution were added through the 4-way stopcock 44 attached to Y-connector 34. The $NaBH_4$ reacted with the residual oxygen on the SFHS molecules causing small bubbles to form in hoses 32 and 50. The oxygen released by the $NaBH_4$ freed more hemoglobin sites for the PLP to attach. Fifteen minutes after the first addition of $NaBH_4$, the remaining $NaBH_4$ was added at a rate of 2 mls per minute. Immediately thereafter, a sample of the pyridoxalated SFHS was collected and the methemoglobin concentration measured. At that time, the nitrogen gas was replaced by 100% oxygen gas, which was introduced to stabilize the hemoglobin molecules and prevent further methemoglobin formation. It also oxidized any remaining sodium borohydride in solution.

The PLP to hemoglobin bond, once made, is stable and not affected by the reintroduction of oxygen. Long term exposure of hemoglobin to $BH_4$ will cause it to develop into methemoglobin. Thus, the reintroduction of oxygen to neutralize the remaining borohydride is critical to making a superior SFHS. The vortex mixing action of the invention allows reactions to be immediately stopped and is responsible for the effectiveness of the system.

After oxygenating for 15 minutes, another sample was drawn from reservoir 10. An assay of the oxygenated solution revealed a 95% oxygen saturation.

The next phase of preparation of modified SFHS was glutaraldehyde treatment to form a stable altered hemoglobin product. This preparation phase is herein referred to as an alteration process rather than a polymerization process because the molecular weights of the final product (16,000) are sufficiently smaller than the molecular weight of normal hemoglobin (65,000) to recommend the use of the word altered as a more accurate term. The alteration treatment required the presence of approximately a 4:1 molar ratio of glutaraldehyde to hemoglobin. The total hemoglobin concentration was adjusted to 7.0±0.1g/dl. A simple dilution of the oxygenated SFHS was accomplished with sterile saline, then prechilled (4° C.) glutaraldehyde solution (2.1% w/w ratio in saline) was added to the diluted hemoglobin solution at a 4:1 molar ratio based upon photometric analysis of the total hemoglobin concentration. The 2.1% glutaraldehyde solution was made from a frozen or thawed 25% stock solution originally stored at −27° C. The stock solution was warmed and made liquid. The number of grams of glutaraldehyde solution needed was calculated using the last measured total hemoglobin concentration in grams/liter, divided by 65,000, then multiplied by four times the molecular weight of glutaraldehyde (100), or 400. A proportioning pump (shown as peristaltic pump 47 in FIG. 1) was attached through tubing to the 4-way stopcock 44 at Y-connector 34. The pump delivered the 2.1% glutaraldehyde solution to the SFHS at 2.0 mls per minute. An incubation period beginning with the initial infusion of glutaraldehyde was continued for a period of time sufficient to supply all the glutaraldehyde solution, during which time the SFHS was continuously mixed by the action of the continuously delivered oxygen gas. After delivery of glutaraldehyde, incubation and mixing continued for an additional period of time sufficient to complete alteration to the targeted value. This additional period varied from about two and one-half to about three hours, depending upon whether the initial SFHS was frozen or fresh, and, if frozen, how long it had been stored. The reactivity of SFHS decreases with storage time.

Reactivity testing was accomplished prior to starting modification by taking 25 mils of SFHS and adding a glutaraldehyde solution (40 times the hemoglobin concentration) to it. The time it took the SFHS to gel into "brick" determined the time to leave the glutaraldehyde in solution.

The alteration reaction of the SFHS was finally stopped by dialyzing at 4° C. against a 0.015 M phosphate buffer at pH 7.4±0.1. The dialysis was carried out with a reverse flow membrane dialysis system 64 attached to the reservoir housing 10 at through-wall connector 18. The membrane dialysis system ultilized an 100 liter tank for closed cycle filtration while minimizing contamination and maintaining a sterile environment for the SFHS. The initial preparation for an 100 liter dialysis solution required a tank with prechilled, deionized water. This was followed by vigorously mixing into the water with a plastic paddle one liter of concentrated phosphate buffer. The liter of concentrated buffer contained monobasic phosphate ($NaH_2PO_4$—$H_2O$). which ultimately formed a 0.015 M solution. Due to the slightly acidic nature of the deionized water, a few mls of 40% NaOH were initially added to the monobasic phosphate salt solution. In order to bring the pH up to 7.4, samples of buffer were measured on a pH meter which had been adjusted against a standard buffer solution at 4° C. Titrating such a large volume of buffer required adding a small amount of 10 N hydrochloric acid (HCl), or 40% sodium hydroxide (NaOH), and vigorously agitating with a paddle to disperse the chemical throughout the tank. Approximately 10 minutes were required for the buffer to equilibrate with the titrant prior to taking another pH sample. Once a pH of 7.4 was obtained, the dialysis pump flow was reduced from 4 liters to about 1 liter per minute. A reverse flow membrane system similar to those used on renal dialysis units was properly positioned in its fitting above the 100 liter tank. Sterile hoses connected a blood (peristalitic) pump with the reverse flow system and with the reservoir 10. The buffered dialysis solution from the 100 liter tank flowed past the outside of the membrane system at 0.8 to 1.0 liters per minute. The output from the dialysis apparatus 64 was returned to the reservoir 10 through a sterile fitting. The unused ports in reservoir 10 were clamped off.

Stopping the system for a refill with fresh buffered dialysate required a certain sequence of events to be accomplished. The first action was to stop the transfer of SFHS from the reservoir 10 to the dialysis equipment by switching off the blood pump. Next the 100 liter tank was drained and refilled with fresh buffered phosphate solution. The reverse flow membrane system was reset and run with this second batch of dialysate. A third batch was then loaded and the process repeated. Since the pH level of the final product was determined by the pH of the third tank of buffered dialysis solution, great care had to be taken to monitor the actual pH level during the dialysis operation. For dialysing 10 or more liters of SFHS against 100 liters of buffer, at least three hours of circulation was necessary. During all times, the hemoglobin concentration had to be monitored so that the SFHS was not concentrated to the point of protein precipitation. When a high protein level (>19 g/dl) was obtained, sterile saline was added to bring the level down to a concentration just slightly above the desired level for the final product. This technique is useful because the addition of sodium and potassium salt solutions in a later step further reduced the SFHS to desired protein levels.

A smooth transition to the final sample preparation phase required that sterilized 500 ml centrifuge bottles with screw cap lids be prepared in advance. After the last dialysis period, the outlet hose from the reverse flow membrane system was removed from the through-wall connector 18 and the output from the outlet hose used to fill the sterile centrifuge bottles with SFHS. When a large volume of modified SFHS was produced, excess stroma fluid was poured into sterile flasks with gauze/aluminum covers for temporary storage at 4° C. Filling other centrifuge bottles from these flasks took place, as is preferable, in a sterile laminar flow hood.

Two components of the solution had to be removed before the next preparation step. A small amount of octanol remained in solution after dialysis, and some large protein aggregates developed as a consequence of the polymerization process. Centrifugation of the solution for 60 minutes at an average relative centrifuge force (RCF) of 8050, with a sedimentation factor, K, of 1660, in sterile, centrifuge bottles placed in a refrigerated centrifuge at 3° C., precipitated the aggregates onto the walls and bottoms of the centrifugation bottles. The octanol rose to the surface of the SFHS where it was removed by aspiration with a pasteur pipet attached to a faucet aspirator. This separation phase of the procedure required that the centrifugation steps be repeated until all the SFHS in the flasks had been spun.

The next preparation step was replenishment of normal salt levels in the SFHS since these were removed by dialysis. SFHS samples were tested in a flame photometer for sodium and potassium ion concentrations. By using a formula based on the total volume of salt in solution, the sodium and potassium levels were adjusted to near physiological levels by the addition of concentrated solution of salts. Since the addition of the salt solution diluted the SFHS, a calculation of the proper dilution factor was needed in order to reach a hemoglobin concentration of 7.0 g/dl. Sterile saline acted as a solvent for the salts. Maintenance of a sterile environment was a prime consideration throughout the entire procedure, so that care was taken to infuse the salt solution into the SFHS via a sterile 0.22 micron filter. As a final precaution, the whole batch was step filtered first through 0.45 micron filters, and then through 0.22 micron filters directly into 1 liter blood bags.

The final modified stroma-free hemoglobin solution prepared as described above was determined to be substantially antigenic and substantially free of methemoglobin. The final product has a $P_{50}$ (50% oxygen saturation pressure) of about 25 mm Hg, and molecular weights of about 16,000, both closely approximating whole blood. In use in test animals, it not only successfully transported oxygen, but met retention time requirements of from 23 to 25 hours.

The disclosed apparatus shows that bubbling creates an ideal environment for mixing small amounts of reagents into solution. The disclosed apparatus allows a dilution factor of 1:1000 over pouring reagents directly into solution and stirring. The apparatus further maintains a positive pressure preserving a sterile environment for the process.

Those with skill in the art will see that the disclosed use of the apparatus may be easily modified to produce, for instance, high concentrations of methemoglobin by not oxidizing the pyridoxalized SFHS. The apparatus may also be modified to produce larger quantities of modified SFHS by scaling up the disclosed embodiment. Those with skill in the art will see that the performance of a scaled up model will be improved by the addition of additional outlets, hoses and Y-connectors similar to elements 18, 32 and 34 in the disclosed embodiment, each of which may be fitted with a 4-way stopcock for supplying reagent. The present embodiment may be modified for the preparation of larger amounts of modified SFHS by replacing Y-connector 42 with Y-connector 66 shown in FIG. 2. A second hose 76 may then be connected from pump 47 to mix reagent with the incoming bubbles.

Those with skill in the art will also see that the functions of the Y-connectors and stopcock of the present embodiment may be performed by alternate structures. For example, production models of the disclosed apparatus may be made as a casting wherein the tubing, connectors, fittings, etc. providing conduits for the flow of gas and solution are cast or machined as part of the primary casting. Similarly, the functions of the solution reservoir and of components of the gaseous separation unit have been performed in some experimental embodiments by long lengths of tubing.

While the word "tube" has been used in the foregoing description in a manner that implies a rigid and straight fluid conduit, as differentiated from a flexible hose, the word "tube" is intended to include all fluid conduits, including a hose, or machined or cast passages through other structures.

It is understood that certain other modifications to the invention as described may be made, as might occur to one with skill in the field of this invention, within the intended scope of the claims. Therefore, all embodiments contemplated have not been shown in complete detail. Other embodiments may be developed without departing from the spirit of this invention or from the scope of the claims.

I claim:

1. An apparatus for mixing reagents into a solution, comprising:
   (a) a solution reservoir;
   (b) a reagent supply;
   (c) first connector means having first, second and third fittings and an infusion port;
   (d) a first stopcock attached to the first connector means through the infusion port;
   (e) a pressurized gas supply;
   (f) first conduit means for delivering pressurized gas from the pressurized gas supply to the first fitting of the first connector means;
   (g) second conduit means for delivering solution from the solution reservoir to the second fitting of the first connector means;
   (h) third conduit means for delivering reagent from the reagent supply to the first stopcock; and,
   (i) fourth conduit means for returning solution from the third fitting of the first connector means to the solution reservoir.

2. The apparatus for mixing reagents into a solution according to claim 1, wherein the fourth conduit means comprises:
   (a) second connector means having first, second and third fittings;
   (b) fifth conduit means for delivering solution from the third fitting of the first connector means to the first fitting of the second connector means;
   (c) sixth conduit means for delivering solution from the solution reservoir to the second fitting of the second connector means; and,
   (d) seventh conduit means for returning solution from the third fitting of the second connector means to the solution reservoir.

3. The apparatus for mixing reagents into a solution according to claim 2, wherein the fourth conduit means further comprises:
   (a) an infusion port on the second connector means;
   (b) a second stopcock attached to the second connector means through the second connector means infusion port; and,
   (c) eighth conduit means for delivering reagent from the reagent source to the second stopcock.

4. The apparatus for mixing reagents into a solution according to claim 2, further comprising means for gaseous separation positioned inside the solution reservoir, the seventh conduit means connecting the third fitting of the second connector means to the gaseous separation means.

5. The apparatus for mixing reagent into a solution according to claim 4, wherein the gaseous separation means further comprises:
   (a) an enclosure having a closed top and an open bottom, the open bottom positioned below the solution level inside the reservoir and the closed top positioned above the solution level, the closed top further having at least one vent hole:
   (b) a hollow perforated bulb positioned inside the enclosure, the seventh conduit means connecting the third fitting of the second connector means to the bulb;
   (c) a permeable membrane adjacent to the perforated bulb; and,
   (d) ninth conduit means for delivering pressurized gas connecting the pressurized gas supply to said enclosure adjacent to the open bottom of said enclosure, whereby the pressurized gas produces bubbles over the perforated bulb.

6. An apparatus for the production of modified stroma-free hemoglobin solution, comprising:
   (a) a first enclosure having an opening and a cover, the cover not fitting gas-tight over the opening;
   (b) stroma-free hemoglobin solution partially filling the first enclosure;
   (c) a first through-wall tube connector mounted through the side of the first enclosure above the fluid level of the stroma-free hemoglobin solution;

(d) second and third through-wall tube connectors mounted through the side of the first enclosure below the fluid level of the stroma-free hemoglobin solution;

(e) a fourth through-wall tube connector mounted through the bottom of the first enclosure;

(f) first connector means positioned below the first enclosure, the first connector means having first, second and third fittings and a first infusion port;

(g) a first tube outside the enclosure connecting the second through-wall tube connector to the first fitting of the first connector means;

(h) a pressurized gas supply;

(i) a second tube connecting the pressurized gas supply to the second fitting of the first connector means;

(j) second connector means positioned below the first enclosure and above the first connector means, the second connector means having first, second and third fittings;

(k) a third tube connecting the third fitting of the first connector means to the first fitting of the second connector means;

(l) a fourth tube outside the first enclosure connecting the third through-wall tube connector to the second fitting of the second connector means;

(m) a fifth tube connecting the third fitting of the second connector means to the fourth through-wall tube connector;

(n) means for gaseous separation positioned inside the first enclosure;

(o) a sixth tube inside the first enclosure connecting the fourth through-wall tube connector to the gaseous separation means;

(p) a seventh tube inside the first enclosure connecting the first through-wall tube connector to the gaseous separation means;

(q) an eighth tube outside the first enclosure connecting the pressurized gas supply to the first through-wall tube connector.

(r) a first stopcock attached through the first infusion port to the first connector means;

(s) means for pumping reagents; and, (t) a ninth tube connecting the pumping means to the first stopcock.

7. The apparatus for the production of modified stroma-free hemoglobin solution according to claim 6, further comprising first and second hose clamps for controlling the delivery of pressurized gas, one each attached to the second tube and to the eighth tube.

8. The apparatus for the production of modified stroma free hemoglobin solution according to claim 6, wherein the gaseous separation means comprises:

(a) a second enclosure positioned inside the first enclosure and having a first opening below the fluid level of the stroma-free hemoglobin solution and having a plurality of smaller openings above said fluid level, wherein the seventh tube connects to the second enclosure adjacent to the first opening:

(b) a hollow perforated bulb positioned inside the second enclosure above the first opening and connected to the sixth tube; and, (c) a foam sheet enclosed by the perforated bulb.

9. A method of mixing reagent into a solution, comprising the steps of:

(a) providing a reservoir for storing the solution:

(b) infusing small amounts of reagent into the solution as the solution is flowed past the infusion point, making a mixed solution, while concurrently supplying pressurized gas to the infusion point;

(c) using bubbles created by the pressurized gas to lift the mixed solution;

(d) mixing the mixed solution with additional solution from the solution reservoir to make a further mixed solution and further bubble-lifting the further mixed solution to return to the solution reservoir.

10. The method of mixing reagent into a solution according to claim 9, further comprising infusing small amounts of reagent into the mixed solution as the solution is flowed past the point where additional solution is mixed with the mixed solution.

11. The method of mixing reagent into a solution according to claim 9, wherein bubble-lifting the further mixed solution to return to the solution reservoir further comprises:

(a) providing a perforated bulb having an adjacent permeable membrane, the bulb being positioned inside an enclosure having an open bottom and closed top, the top having at least one vent hole, the enclosure further being positioned inside the solution reservoir;

(b) bubble-lifting the further mixed solution to the inside of the perforated bulb; and, (c) bubbling gas bubbles over the outside of the perforated bulb.

* * * * *